(12) United States Patent
Wong et al.

(10) Patent No.: US 11,723,993 B2
(45) Date of Patent: *Aug. 15, 2023

(54) ULTRAVIOLET DISINFECTION APPARATUS

(71) Applicant: Soulnano Limited, Hong Kong (HK)

(72) Inventors: Cho Hang Wong, Hong Kong (HK);
Hung Hsin Hsieh, Kaohsiung (TW);
Pui Yan Wong, Hong Kong (HK); Kai Lai Chan, Hong Kong (HK)

(73) Assignee: Soulnano Limited, Hong Kong (HK)

( * ) Notice: Subject to any disclaimer, the term of this patent is extended or adjusted under 35 U.S.C. 154(b) by 373 days.

This patent is subject to a terminal disclaimer.

(21) Appl. No.: 17/037,782

(22) Filed: Sep. 30, 2020

(65) Prior Publication Data

US 2021/0260228 A1 Aug. 26, 2021

Related U.S. Application Data

(63) Continuation-in-part of application No. 16/986,299, filed on Aug. 6, 2020.

(Continued)

(51) Int. Cl.
*A61L 2/10* (2006.01)
*C02F 1/32* (2023.01)
*A23L 3/28* (2006.01)

(52) U.S. Cl.
CPC ............... *A61L 2/10* (2013.01); *A23L 3/28* (2013.01); *C02F 1/325* (2013.01);
(Continued)

(58) Field of Classification Search
CPC .................................... A61L 2/10; A23L 3/28
See application file for complete search history.

(56) References Cited

U.S. PATENT DOCUMENTS

2005/0263716 A1\* 12/2005 From ............... C02F 1/325
250/453.11
2006/0131246 A1\* 6/2006 Ehlers ............... C02F 1/325
210/748.11

(Continued)

FOREIGN PATENT DOCUMENTS

CN 203976438 U 12/2014
CN 107074590 A 8/2017
(Continued)

OTHER PUBLICATIONS

International Search Report and Written Opinion of corresponding PCT Application No. PCT/CN2021/073640 dated Apr. 23, 2021.

*Primary Examiner* — Omar Flores Sanchez
(74) *Attorney, Agent, or Firm* — Idea Intellectual Limited; Margaret A. Burke; Sam T. Yip

(57) ABSTRACT

An ultraviolet disinfection apparatus being integral to existing pipe system is provided, comprising a hollow body with at least two open ends and an arbitrary cross-section, a UV module and a control module. The hollow body is configured for receiving the UV module, and to communicate with at least one end of a pipe structure such that a medium passing therethrough will not leak. The hollow body has an inner surface and an outer surface; the inner surface includes one or more interior structures defined by one or more partition walls for sub-dividing hollow space of the hollow body into at least two relatively smaller hollow spaces. The UV module comprises one or more UV LED arrays arranged independently or severally on the inner surface and/or the interior structures to increase UV exposure to the medium. The control module is remotely connected to the UV module outside the hollow body.

18 Claims, 7 Drawing Sheets

Related U.S. Application Data

(60) Provisional application No. 62/979,383, filed on Feb. 20, 2020.

(52) U.S. Cl.
CPC ... *A61L 2202/14* (2013.01); *C02F 2201/3222* (2013.01); *C02F 2303/04* (2013.01)

(56) References Cited

U.S. PATENT DOCUMENTS

| | | | |
|---|---|---|---|
| 2013/0236353 A1* | 9/2013 | Blechschmidt | C02F 1/325 |
| | | | 422/4 |
| 2014/0131286 A1 | 5/2014 | Basu et al. | |
| 2016/0271280 A1* | 9/2016 | Liao | G06F 3/0393 |
| 2017/0166458 A1* | 6/2017 | Rimbault | A23L 2/50 |
| 2017/0280737 A1* | 10/2017 | Liao | C02F 1/325 |
| 2019/0142981 A1* | 5/2019 | Kim | G01B 11/02 |
| | | | 250/455.11 |
| 2020/0405895 A1* | 12/2020 | Mock | B08B 9/08 |
| 2021/0259451 A1* | 8/2021 | Wong | A23L 3/28 |
| 2022/0160914 A1* | 5/2022 | Liu | A61B 90/70 |
| 2022/0214069 A1* | 7/2022 | Nuno | F24F 8/22 |
| 2022/0341086 A1* | 10/2022 | Jang | D06F 58/22 |

FOREIGN PATENT DOCUMENTS

| | | | |
|---|---|---|---|
| CN | 109956517 A | 7/2019 | |
| JP | 2014161767 A | 9/2014 | |
| JP | 2014221445 A | 11/2014 | |
| WO | 2009072220 A1 | 6/2009 | |

* cited by examiner

ULTRAVIOLET DISINFECTION APPARATUS

CROSS-REFERENCE TO RELATED APPLICATIONS

This application claims priority from (1) U.S. provisional patent application No. 62/979,383 filed on Feb. 20, 2020; and is a continuation-in-part of (2) U.S. non-provisional patent application Ser. No. 16/986,299 filed on Aug. 6, 2020, and the disclosures of which are incorporated herein by reference in their entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to an ultraviolet (UV) disinfection apparatus, more particularly to an UV disinfection apparatus that is able to apply to a pipe system.

BACKGROUND OF THE INVENTION

Ultraviolet (UV) treatment eliminates bacteria, viruses, spores and mold in the fluid such as water and air fluid, which works similar to the way of the strong sunlight (UV-A, UV-B); and UV-C wavelength is particularly useful to inactivate pathogens that it is completely absorbed by oxygen molecules and never reaches the Earth's surface. UV lamp are generally designed to destroy the DNA or RNA of these micro-organisms. The bonds that link the RNA or DNA chain together rupture when exposed to light with the wavelengths of about 220 to 310 nm.

Conventional UV sources include fluorescent gas discharge tubes or lamps, and most of them are with a low or medium pressure mercury vapor medium for the gas discharge. The drawbacks of these fluorescent gas discharge type UV sources include the hazard of the mercury in the tubes, risks of breakage, narrow spectral range, low power efficiency, some are very sensitivity to the variations of the temperature, and difficulties in maintenance and cleaning.

UV light emitting diodes (LEDs) have been developed lately, and the use of UV LEDs also has many advantages including a wider UV band with multiple LED wavelengths, which can offer a high-power output with less power consumption than fluorescent type UV lamps. UV LEDs also have greater longevity, power up more quickly without requiring a delay time built into the system for the UV light source to reach its optimum UV energy output, and do not contain mercury.

Accordingly, there are many UV LED sanitation and disinfection systems and/or devices for water or air. However, most of them are stand-alone unit that are incorporated into existing pipe-system. Also, most of them do not have the same temperature and quality concerns as for processing temperature-sensitive medium, e.g., food or beverage. The U.S. FDA has approved UV-C radiation, a low-temperature radiation, for treatment of juice products to reduce human pathogens and other microorganisms. UV-C treatment can be carried out at low temperature and is regarded as a non-thermal method. During UV-C treatment, it seems that no known toxic or significant non-toxic by-products are formed; certain contaminants can be removed; and no significant loss of flavor or odor is removed from the food or beverage. In addition, most of the conventional UV LED sanitation and disinfection systems are stand-alone unit that cannot be incorporated into existing pipe-system. Redesigning or retrofitting a UV disinfection device can be costly, space restrictive, and make system unable to operate at its optimum level according to the initial setting thereof. Therefore, there is a need to develop a new UV LED disinfection device that is easy to operate and integrate into the existing pipe system.

SUMMARY OF THE INVENTION

According to an aspect of the present invention, an ultraviolet (UV) disinfection apparatus with a hollow section is provided, which is able to be a new fluid-flow pipe design or integrated/installed in most of the existing pipe systems.

According to an embodiment of the present invention, the UV disinfection apparatus comprises a hollow body having an arbitrary cross-section and at least two open ends, a UV module and a control module. The hollow body of the apparatus is configured for receiving the UV module; each of the at least two open ends communicates with one end of a pipe structure, e.g., inlet/outlet of a pipe. The hollow body further comprises at least an inner surface and an outer surface. The inner surface may include one or more interior structures which can be flat or curved. The interior structures are defined by one or more partitions situated in part or in full length along the inner surface of the hollow space. On each of the interior structures, there can be configured to receive the UV module. The UV module comprises a plurality of UV LED arrays which can be independently or severally arranged with each other, and one or more of the UV LED arrays is/are mounted on the flat or curved surface of the interior structures. The control module is connected to the UV module and is located remotely from the hollow body of the apparatus.

In one embodiment, the outer surface of the hollow body of the apparatus is configured to receive one or more heat dissipating elements for dissipating the heat from inside to outside of the hollow body in order to keep the temperature in the hollow body constant throughout the operation of the apparatus.

In another embodiment, the arbitrary cross-sections along the hollow body are uniform. More specifically, the uniform arbitrary cross-sections along the hollow space are in polygonal shape, e.g., octagonal shape. Other arbitrary shapes are also possible for the uniform cross-sections along the hollow body of the apparatus, as long as one or both ends of the hollow body correspond to the cross-section of one end of a pipe to be connected therewith so that any medium passing through the connection between the pipe and the hollow body of the apparatus will not leak out.

In other embodiment, the one or more partitions are one or more inter-cross supporting elements being situated in part or in full length along the inner surface of the hollow body. More specifically, the one or more inter-cross supporting elements are mounted on at least two points on the inner surface of the hollow body so that the hollow space of the hollow body is sub-divided into at least two relatively smaller hollow spaces, wherein on each of the inner surface of the hollow body and surfaces of the inter-cross supporting elements there is mounted with a plurality of UV LED arrays arranged independently or severally with each other so that the intensity and uniformity of the UV lights reaching the medium passing through the hollow body of the apparatus are higher than those from the UV LED arrays simply mounted on the inner surface of the hollow body without any sub-division by the partitions.

In one embodiment, the inner surface of the hollow body is UV-reflective. By coated with or formed by UV reflective materials of the inner surface, the higher reflectance of the UV lights can increase the disinfection efficiency.

In another embodiment, the present apparatus further comprises an inner pipe structure situated in the interior of the hollow body of the present apparatus, where the medium can pass through the interior space of the inner pipe structure while the UV lights from the UV LED arrays can pass through the wall of the inner pipe structure without any loss of energy to disinfect the medium.

In the present invention, the medium passing through the hollow body of the apparatus includes but not limited to gas, liquid and solid, or any combination thereof.

The present invention has various applications including, but not limited to, air treatment, freshwater and wastewater treatments, disinfection procedure in food processing/industry, etc.

In one example, a food and beverage processor is provided comprising at least one pipe structure and the apparatus of the present invention for disinfecting an edible medium passing through a connection between said at least one pipe structure and the present apparatus by UV radiation from the UV module of the apparatus while the flow rate of the edible medium and operational temperature of the processor remains constant throughout the disinfecting process of the edible medium.

In another example, a plumbing and drainage system is provided comprising at least one pipe structure and the present apparatus for disinfecting a medium passing through a connection between said at least one pipe structure and the present apparatus by UV radiation from the UV module of the apparatus while the flow rate of the medium and the temperature of the plumbing and drainage system remains constant throughout the disinfecting process of the medium.

Yet another example is a disinfection system comprising at least one pipe structure and the present apparatus for disinfecting a medium passing through a connection between said at least one pipe structure and the apparatus of the present invention by UV radiation from the UV module of the apparatus while the flow rate of the medium and the temperature of the disinfection system remains constant throughout the disinfecting process of the medium, wherein said medium comprises gas, liquid, solid, or any combination thereof.

The present invention is also applicable in a method for disinfecting an edible medium in a manufacturing process thereof comprising exposing the edible medium to a UV source during transportation from a pipe structure to another pipe structure of a food or beverage processor through a connection between two pipe structures, wherein the connection comprises the present apparatus.

The present invention is also useful in disinfecting a medium during wastewater or sewage treatment comprising exposing the medium to a UV source during transportation from a pipe structure to another pipe structure of a wastewater or sewage treatment system through a connection between two pipe structures, wherein the connection comprises the present apparatus.

BRIEF DESCRIPTION OF THE DRAWINGS

Embodiments of the present invention are described in more detail hereinafter with reference to the drawings, in which.

DETAILED DESCRIPTION

Embodiments of the present invention herein provide an apparatus incorporating ultraviolet (UV) light emitting diodes (LEDs) for disinfection of the medium passing therethrough including but not limited to drinking water, sewage water, food and beverage such as milk, juice, soft drinks, beer, and any other food need to be disinfected before consumption in food industry. The apparatus described herein allows integration into an existing fluid pipe without any structural modification. The UV LEDs are arranged into array to form UV LED array in any pattern such as radial and/or longitudinal arrangement, and the number and/or density of UV LEDs in each array can vary according to the actual application thereof.

Figure 1:
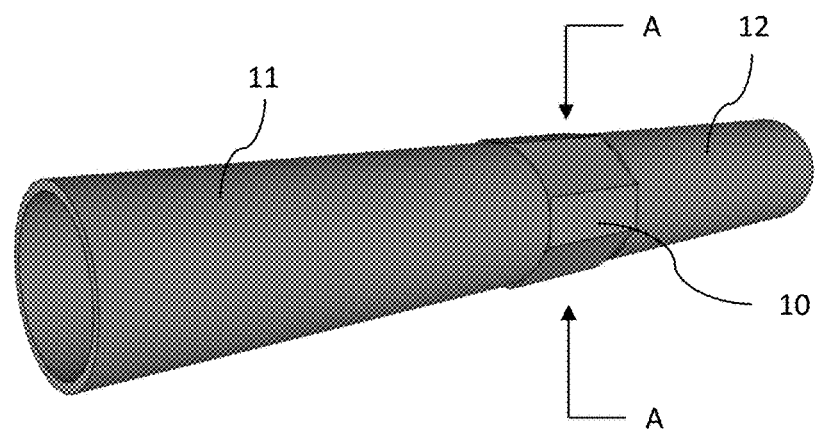
FIG. 1 is a schematic diagram illustrating the present UV disinfection apparatus installed between two pipe structures in accordance with an embodiment of the present invention.

With reference to FIG. 1, the present UV disinfection apparatus can be installed between two pipe structures in order to form a connection between the two pipes by connecting one end of the apparatus 10 to one end of a first pipe 11 and connecting another end of the apparatus 10 to one end of a second pipe 31.

Figure 2A:
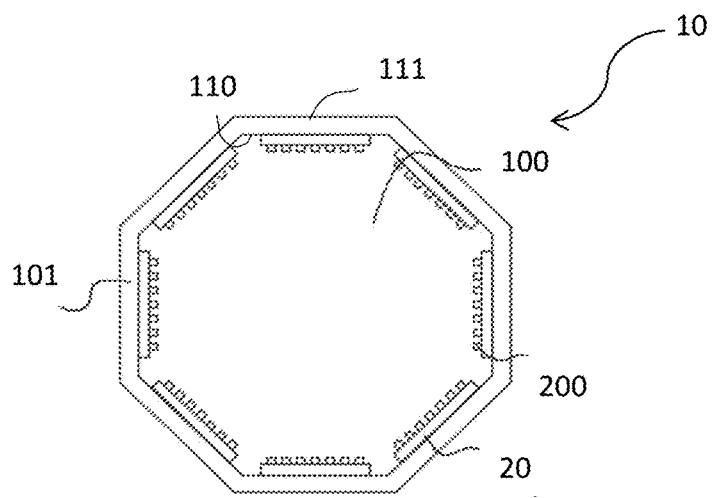
FIG. 2A depicts a cross-section of the present apparatus as shown in FIG. 1 in accordance with an embodiment of the present invention.
Figure 2B:
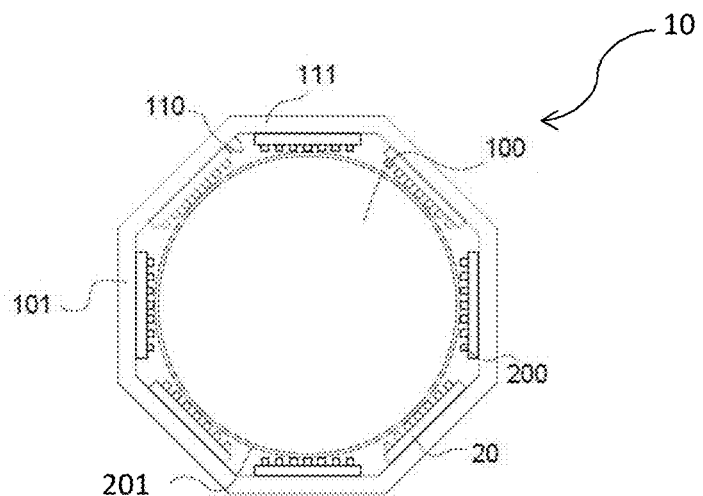
FIG. 2B depicts the cross-section of the present apparatus as shown in FIG. 1 in accordance with another embodiment of the present invention.

With reference to FIGS. 2A and 2B, the apparatus 10 shown in FIG. 1 is illustrated in more detail from a cross-sectional view of the A-A cross-section thereof, wherein the apparatus 10 comprises a hollow body 101, a UV module 20 and a control module 30. The UV module 20 is received on the inner surface 110 of the hollow body 101 and comprises a plurality of UV LED arrays 200. Each of the UV LED arrays 200 is mounted on the inner surface 110. The control module 30 is electrically connected to the UV module 20, and is located outside the polygon body 10. In a preferred embodiment, the inner surface 110 is UV-reflective, e.g., with a UV-reflective coating thereon. In another embodiment, the present apparatus further comprises an inner pipe 201, as shown in FIG. 2B, for carrying the liquid passing through the present apparatus. Because the fluid passing through the inner pipe 201 needs to be exposed to the UV light from the UV LED arrays, it is preferably made of a material that allows UV light to pass through without substantially reducing the energy of the UV light when it reaches the fluid passing through the inner pipe 201. For example, the inner pipe 201 can be made of quartz; the fluid passing through the inner pipe is a liquid with substantially part or all of the ingredient(s) extracted from a source, and with or without suspended solids. For example, the liquid can be a juice or juice-like liquid; the source of the ingredients being extracted can be any fruit, vegetables, nuts, beans, leaves, plants and/or any sources that are edible. The incorporation of an inner pipe into the hollow body of the present apparatus for fluid to pass through can also apply in other embodiments of the present invention without being limited to this particular embodiment.

Figure 3:
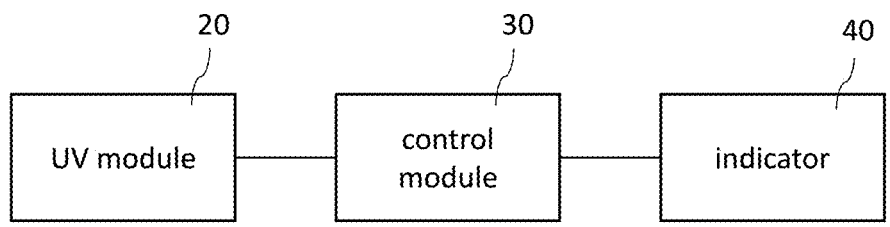
FIG. 3 is a block diagram illustrating the present UV disinfection apparatus in accordance with an embodiment of the present invention.

Exposure to UV radiation is known to be a cause of skin cancer. Therefore, as shown in FIG. 3, an indicator 40 is added to the apparatus capable of generating signal to indicate to or warn the operators or users of the apparatus that the UV module 20 is operating or there is an object, e.g., human being or other creature, approaching the apparatus while the UV module 20 is in operation, especially where the present UV disinfection apparatus is designed to be installed at the inlet or the outlet of the pipe system. The warning signal from the indicator 40 may be an audio, e.g. a sound from a buzzer, a visual, e.g., a blinking light from an LED, or both, or any other signal. Some signals can be an input/output signals that would be digital or analog for indications in other systems or parts such as valves or pumps in order to generate an emergency stop function for the entire system.

In the present invention, the shape of the hollow body 101 accords to the shape of the arbitrary cross-section, which can be triangular, square, or polygonal including pentagonal, hexagonal, and octagonal, and the inner surface 110 of the hollow body 101 should enable the one or more UV LED arrays 200 to be mounted thereon. The mounting of the UV LED arrays 200 on any of the inner surface and/or surfaces of any partitioning elements can be achieved by welding, molding, or any conventional method which secures the UV LED arrays onto said surface. The afore-mentioned surface or surfaces where the UV LED arrays are mounted thereon can be flat or curved.

Figure 4:
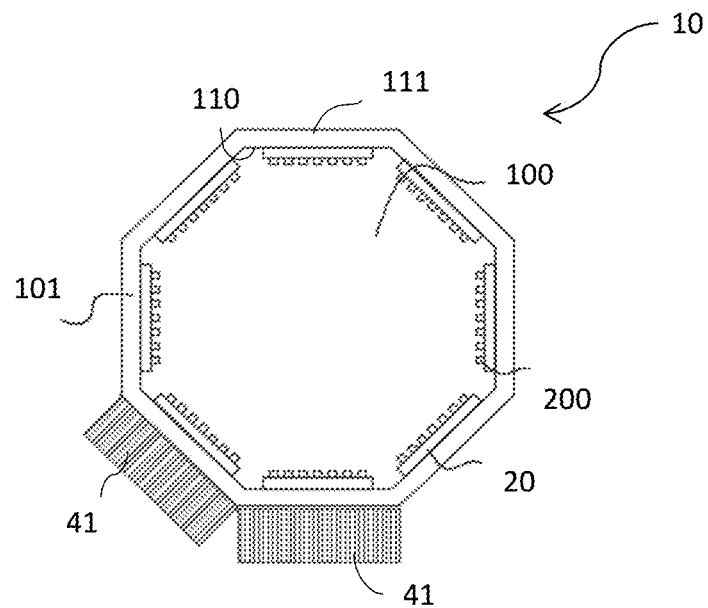
FIG. 4 is a schematic diagram illustrating the present UV disinfection apparatus having heat dissipation elements mounted on the hollow body of the apparatus in accordance with an embodiment of the present invention.

With reference to FIG. 4, the present UV disinfection apparatus further comprises heat dissipating elements being mounted on the outer surface of the hollow body of the apparatus. In this example, the heat dissipating elements 41 may be one or more heat sinks. The heat dissipating elements 41 are mounted on a flat outer surface 111 of the hollow body 101. Alternatively, because the UV LED arrays 200 being mounted on the inner surface 110 of the hollow body 101 generates a relatively large amount of heat during its operation, the heat dissipating elements 41 may further include a liquid-cooling system (not shown in FIG. 4) that allows external cooling liquid such as cold water, to flow through at least a portion of the outer surface 111 and the heat sinks, and it may further flow through the hollow body 101 of the apparatus 10, while the cooling liquid is isolated from the medium passing through the hollow space of the hollow body to the pipe structure.

Figure 5:
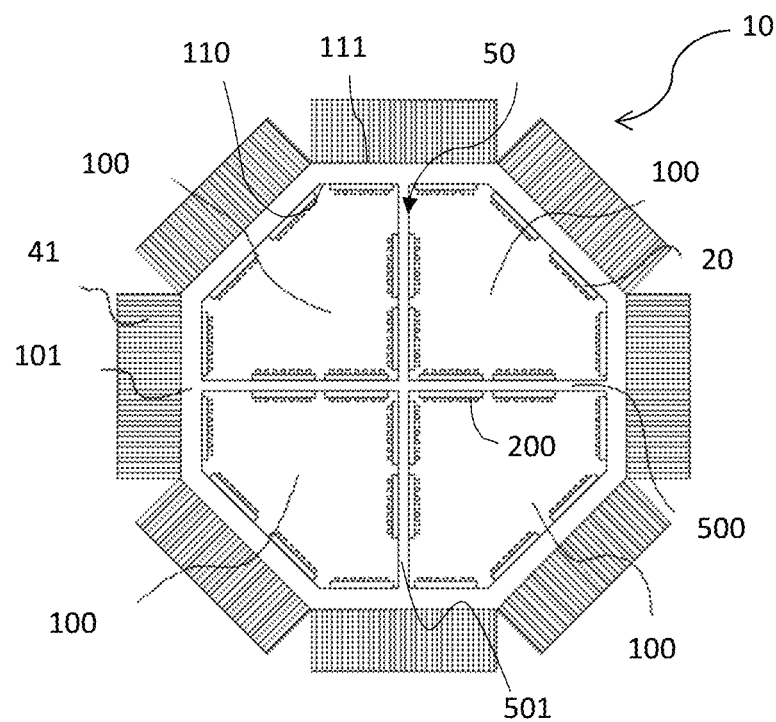
FIG. 5 is a schematic diagram illustrating the present UV disinfection apparatus in accordance with another embodiment of the present invention.

With reference to FIG. 5, the present UV disinfection apparatus further comprises partitioning elements to sub-divide the hollow space 100 of the hollow body 101 into four relatively smaller hollow spaces to increase the intensity and density of the UV LED arrays along the hollow body for disinfecting some semi-transparent or less transparent fluids such as juice and wine, because the fluids contain some substances which lower the light transmittance, thus UV light from the UV LEDs of the UV LED arrays cannot travel for a long distance in the hollow space of the hollow body, therefore shortening the travelling distance of the UV light is needed. FIG. 5 shows an embodiment of how an inter-cross supporting element 50 incorporated into the hollow body of the apparatus can improve the disinfection efficiency by the UV LED arrays without affecting the flow rate of the semi-transparent or less transparent fluids passing through the apparatus.

In this example, as shown in FIG. 5, the present UV disinfection apparatus further comprises a partitioning element 50. The partitioning element 50 is formed inside the hollow body 101 with two partition walls (500, 501) each of which being extended from the two opposite sides of the inner surface 110 of the hollow body 101. The two partition walls (500, 501) intersect with each other at the central axis of the hollow body 101 in order to form an inter-cross supporting element which physically sub-divide the hollow space 100 into four equal size smaller hollow spaces. The UV LED arrays 200 are mounted on each surface of the partition walls (500, 501). Because the partition walls are relatively thin, the partitioning element 50 formed therefrom in the hollow body 101 would not occupy a lot of space in the hollow space 100 such that fluid passing through the hollow body will not be slowed down by the partitioning element.

Furthermore, the apparatus in FIG. 5 also comprises heat dissipating elements 41 (e.g., heat sink) being mounted on the outer surface 111 of the hollow body 101, as in FIG. 4. The number of heat dissipating elements mounted on the outer surface 111 of the hollow body 101 can vary according to the number of UV LED arrays 200 installed inside the hollow body 101 and/or the amount of heat dissipated from the UV LED arrays. As it can be seen from FIG. 5, there are some UV LED arrays on the partitioning element 50 which are not adjacent to the heat dissipating elements, and thus there may be chances that the heat generated from those UV LED arrays cannot be efficiently dissipated. In this regard, the partitioning element 50 and the hollow body 101 may be made from a material having good thermal conductivity which is able to dissipate the heat generated from the UV LED arrays 200 to the heat dissipating elements 41.

Figure 6:
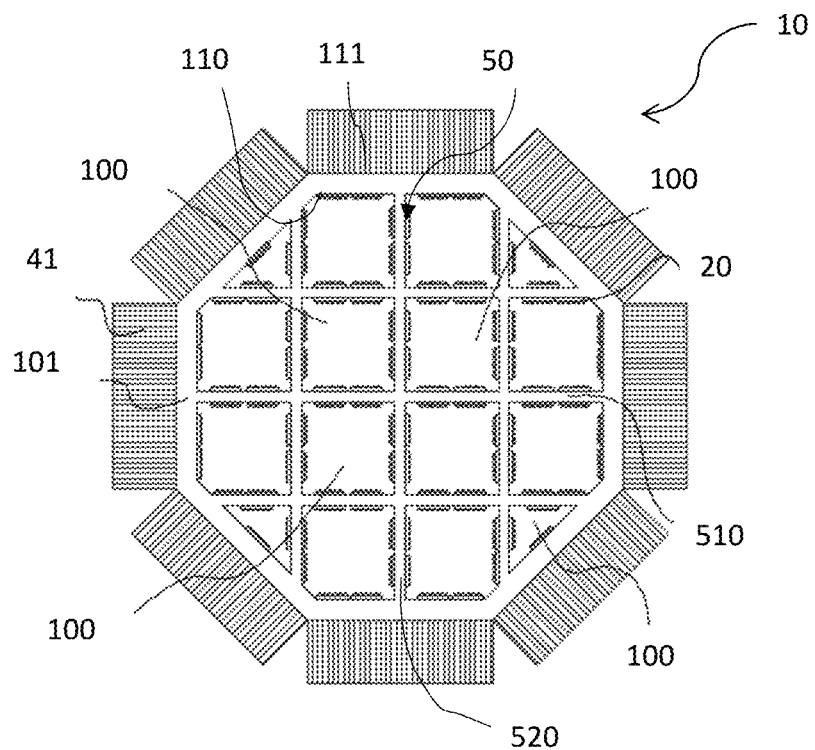
FIG. 6 is a schematic diagram illustrating the present UV disinfection apparatus in accordance with yet another embodiment of the present invention.

With reference to FIG. 6, the present UV disinfection apparatus further comprises a partitioning element for disinfecting a relatively larger volume, higher flow rate, and/or more concentrated fluid pass through the apparatus. In this example, the partitioning element 50 comprises three horizontal partition walls 510 and three vertical partition walls 520, where each of them is extended from the hollow body of the apparatus, and the three horizontal partition walls 510 are arranged in parallel and spaced apart equidistantly; the three vertical partition walls 520 are arranged in parallel and spaced apart equidistantly, and the three horizontal partition walls 510 intersect with the three vertical partition walls 520, where each of the horizontal partition walls 510 is perpendicular to the corresponding vertical partition wall 520 in this example.

It can be understood that in the formation of the partitioning element 50, according to the requirements for UV disinfection, the number of horizontal and vertical partition walls can vary, and the number of the horizontal partition walls can be different from the number of the vertical partition walls. In some other embodiments, the distance between one pair of vertical or horizontal walls can be different from the distance between another pair of vertical or horizontal walls. In other words, the horizontal or vertical walls in the case of three aligned in parallel do not necessarily space apart equidistantly. Also, the angle at the intersection between a horizontal partition wall and a vertical partition wall is not necessarily at 90°, that is, the angle at said intersection can be smaller or larger than 90°.

Figure 7:
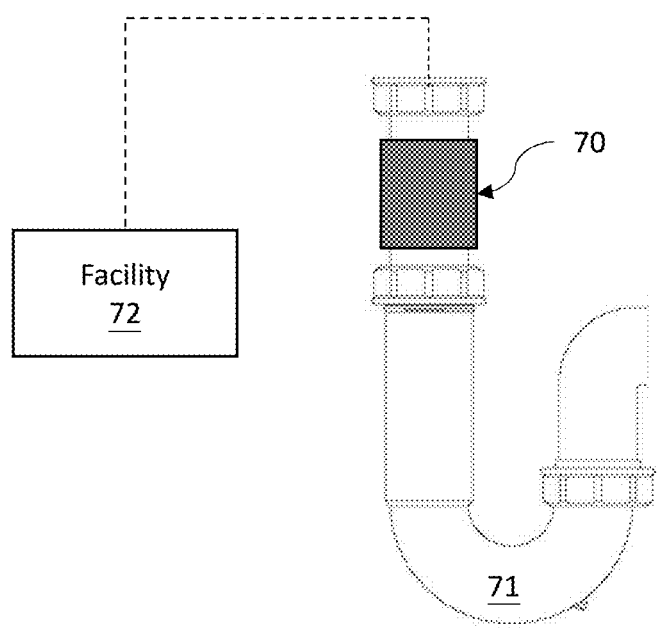
FIG. 7 is a schematic diagram illustrating a potential application of the present UV disinfection apparatus.

With reference to FIG. 7, FIG. 7 is an exemplary diagram illustrating an embodiment of using the UV disinfection apparatus of the present invention. Back to year 2003 as the severe acute respiratory syndrome (SARS) outbreak, at the Hong Kong Amoy Gardens housing estate, there were more than 300 infections and 42 deaths after defective plumbing allowed the virus to spread through the building (http://www.globalconstructionreview.com/news/people-tall-buildings-could-face-extra-covid-19-ri/). In general, every toilet, sink and floor drain have a U-shaped pipe, each U-shaped pipe holds water in its bend which prevents sewer gases from entering the home and allows waste water and odors to escape. When the U-shaped pipe was not filled with water, the air in the discharge pipe of the bathroom can enter the indoor environment. Especially once the extraction fan in the bathroom is turned on.

The UV disinfection apparatus 70 of the present invention can be installed in between the U-shaped pipe 71 and the facility 72 such as toilet. The UV disinfection apparatus 70 can be turned ON to perform bacterial or viral disinfection.

The example illustrated in FIG. 7 can also be incorporated into some conventional air vent pipes in some buildings to avoid the potential health-threatening airborne disease arising from air or so-called aerosolized particles due to the wake effect (a recent news report in South China Morning Post on Mar. 15, 2020 about the spread of Covid-19 virus due to wake effect: haps://www.scmp.com/news/hong-kong/health-environment/article/3075275/coronavirus-eight-more-households-evacuated-hong). It can also be applied in sewage treatment plant for disinfecting potential health-threatening microbes before some wastewater is discharged to the public streams or water (Covid-19 virus found in many sewage points in many countries recently, for example, one of the articles published by American Association for the Advancement of Science on Apr. 21, 2020: https://www.sciencemag.org/news/2020/04/coronavirus-found-paris-sewage-points-early-warning-system).

Figure 8:
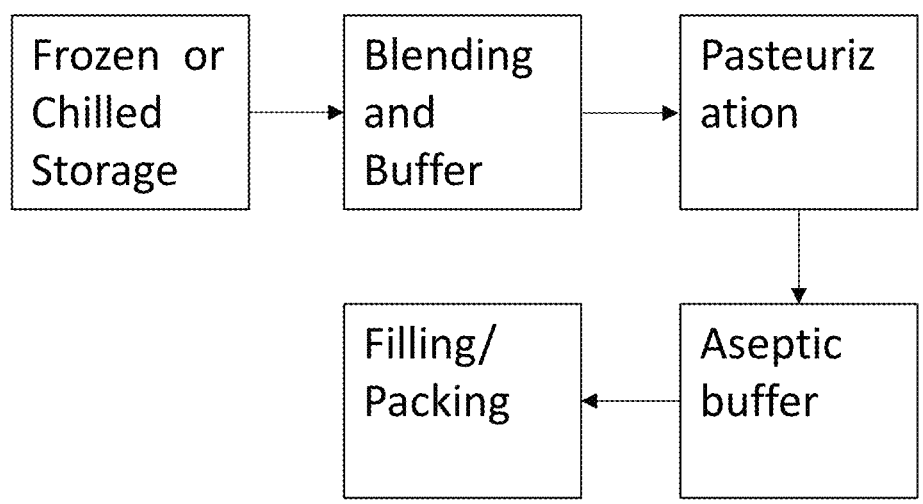
FIG. 8 schematically illustrates an example of a conventional food processing industrial setup and workflow for producing fruit juice.

FIG. 8 illustrates how a conventional food processing industry may be operating in terms of fruit juice production, either from fresh or frozen source of fruits. The most common way of disinfecting the fruit juice after certain extractions is by pasteurization, e.g., at 78° C. for 15 seconds. However, during transportation from one processing place to another in the whole production pipeline, the extracts from the fruit source could be contaminated during transportation, and therefore even it is eventually pasteurized, the quality of the fruit juice extracts may already be deteriorated. The present invention can be used to incorporate into any of the parts of the whole production pipeline at where there may be pipes connecting between any two of the processing places.

Figure 9A:
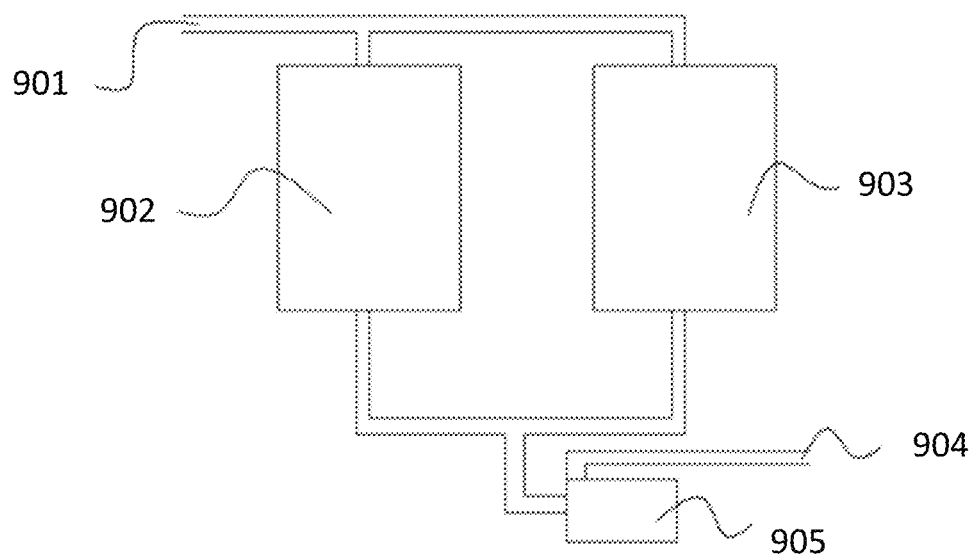
FIG. 9A schematically illustrates a basic design of a food processing system without the present invention.
Figure 9B:
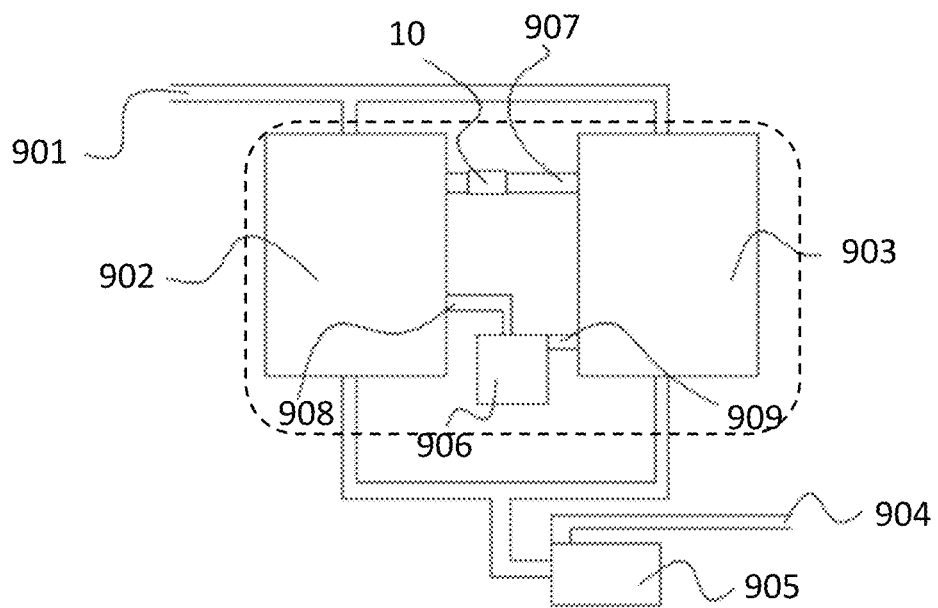
FIG. 9B schematically illustrates a food processing system incorporated with the present apparatus according to an embodiment of the present invention.

FIG. 9A illustrates a setup of a basic food storage system while FIG. 9B illustrates a setup of a food storage system incorporated with the present apparatus.

With reference to FIG. 9A, it can be seen that from the inlet (901) of the food or fluid extracted from the food processing plant, the food or fluid could be stored in a first storage compartment (902) or a second storage compartment (903), and the food or fluid could be pumped by a pump (905) from any or both of the two storage compartments through pipe structures to the outlet (904).

With reference to FIG. 9B, apart from the structures illustrated in FIG. 9A, the two storage compartments (902, 903) are further incorporated with the present apparatus (10) into the pipe connection (907) between the two storage compartments to disinfect the food or fluid communicated between the two storage compartments. Apart from the pump (905) for pumping the food or fluid to the outlet (904), to facilitate the communication of the food or fluid between the two storage compartments, an additional pump (906) is incorporated between the two storage compartments connected with an inlet (908) and an outlet (909) of the additional pump (906) to communicate between the first storage compartment (902) and the second storage compartment (903), respectively. The food or fluid is pumped by the additional pump (906) from the first storage compartment (902) through the inlet (908) to the second storage compartment (903) through the outlet (909). Although it is not shown in FIG. 9B, it is understood that the present apparatus can be incorporated into any pipe structure within the system to play the role of disinfection. Because the present apparatus utilizes UV light to disinfect the medium passing therethrough, there is only a very minimal heat or substantially no heat generated during the disinfection in the presence of some heat sinks or cooling mechanism available in certain embodiments, the food or fluid during the storage procedure would not be deteriorated due to heat generated during disinfection by some conventional methods such as pasteurization. It is important to some temperature-sensitive food or beverage.

Figure 10:
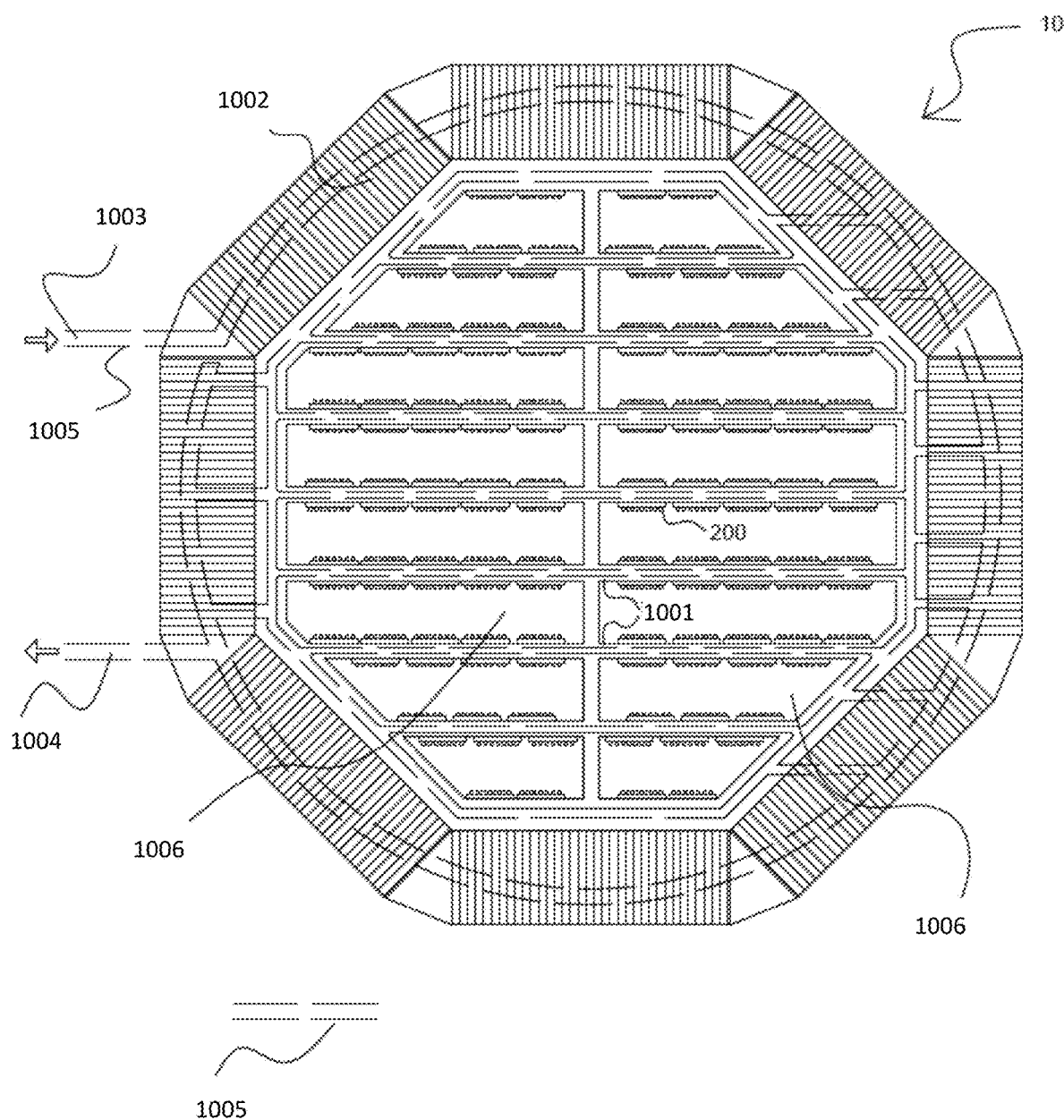
FIG. 10 schematically illustrates an embodiment of the present apparatus being configured for disinfection of medium flowing therethrough in food processing or storage applications.

FIG. 10 illustrates from a cross-sectional view of an embodiment of the present apparatus (10) applied in food processing or storage. In this embodiment, the present apparatus is configured to partition the hollow space of the hollow body in a way that the distance between each parallel pair of horizontal partition walls 1001 is defined such that the UV intensity and dose are sufficient to disinfect the medium 1006 flowing therethrough while the flow rate of the medium remains unchanged. To ensure an efficient disinfection of the medium flowing through the present apparatus while the flow rate thereof is unaffected, a plurality of high power UV LED arrays 200 are used in this embodiment. However, the high power UV LED arrays 200 will generate heat conductive to the partition walls 1001 adjacent to the UV LED arrays 200. To lower the temperature of the partition walls 1001, one or more heat dissipating elements is/are incorporated onto the outer surface of the hollow body connecting the partition walls 1001 so as to enclose the hollow body. Because the material of the hollow body and the partition walls 1001 is thermally conductive, the one or more heat dissipating elements 1002 incorporated onto the outer surface of the hollow body is/are capable of dissipating the heat generated from the high power UV LED arrays 200 through the partition walls 1001 then to the outer surface of the hollow body. The one or more heat dissipating elements 1002 include one or both of passive heat dissipating element (e.g., heat sink) and active heat dissipating element (e.g., water-based cooling system with liquid-cooling inlet 1003, liquid-cooling outlet 904 and cooling pipe 1005). Therefore, the temperature of the medium flowing through the present apparatus will remain unchanged even though the high power UV LED arrays are used. Apart from the configuration illustrated in FIG. 10, it is possible to incorporate other heat dissipating element(s) into the present apparatus in any way that can efficiently dissipate the heat generated from the UV LED arrays without disturbing the flow rate of the medium flowing therethrough.

The flow rate of the medium may also be affected by other factors such as the viscosity and/or size of solid suspensions in the medium flowing through the present apparatus. For media with lower viscosity and/or relatively larger size of the solid suspensions, the average diameter across the cross-section of the hollow body of the present apparatus can be larger than that for media with higher viscosity and/or relatively smaller size of the solid suspensions. Any other means and/or configuration that can assist the flow rate of the medium flowing through the present apparatus is possible to be incorporated into the present apparatus, while the temperature of the medium flowing therethrough is not affected by such incorporation of the means or configuration.

In some embodiments, the medium flowing through the present apparatus includes, but not limited to, liquid food (e.g., liquid egg products), milk, cider, juices, tropical fruit and the extract thereof, vegetable juices or extract.

In other embodiment, the medium flowing through the present apparatus includes, but not limited to, sewage, freshwater, underground water, sea water, wastewater, air, gas, liquid with solid suspension, organic or inorganic compound in liquid state or semi-liquid state, transparent or semi-transparent or substantially non-transparent liquid, and any substance with fluidity.

In other potential applications, for example, air treatment, because the present apparatus utilizes an enclosure design, the conventional HVAC (Heating, Ventilation and Air Conditioning) systems of public transport and hospitals using UV-C as a source of disinfection with the incorporation of the present apparatus can be operated continuously without potential safety concerns on human beings.

The present apparatus can also be used in combination with other systems to disinfect the medium passing therethrough. For example, the incorporation of some anti-bacterial agents such as zinc oxide, silicon oxide and titanium dioxide into the present apparatus can provide additional chemical treatment to the medium passing therethrough because some of these anti-bacterial agents are photocatalytic under the exposure to high energy bandgap EM waves.

The foregoing description of the present invention has been provided for the purposes of illustration and description. It is not intended to be exhaustive or to limit the invention to the precise forms disclosed. Many modifications and variations will be apparent to the practitioner skilled in the art. The embodiments were chosen and described in order to best explain the principles of the invention and its practical application, thereby enabling others skilled in the art to understand the invention for various embodiments and with various modifications that are suited to the particular use contemplated.

INDUSTRIAL APPLICABILITY

The present invention is applicable in various fields including, but not limited to, air treatment, freshwater and wastewater treatment, food processing, etc. More specifically, the present invention can be incorporated into any conventional HVAC system, air or water pipe systems in public utilities, airplanes, cruises, or in buildings, as part of the food processing system such as juice disinfection in compliance with US FDA standard and food storage.

What is claimed is:

1. An ultraviolet disinfection apparatus comprising:
   a hollow body comprising a cross-section and at least two open ends, each of the at least two open ends communicating with one end of a pipe structure, and further comprising an inner surface and an outer surface, the inner surface including one or more interior structures which is flat or curved, the one or more interior structures being defined by one or more partitions situated in part or in full length along the inner surface of the hollow space;
   an ultraviolet (UV) module comprising one or more UV LED arrays independently or severally arranged with each other, the one or more UV LED arrays being mounted on the flat or curved surface of the interior structures; and
   a control module being connected to the UV module and located remotely from the hollow body of the apparatus;
   wherein the one or more interior structures is a partitioning element defined in a hollow space of the hollow body and extended from one end to another end of the inner surface of the hollow body to form at least one vertical or horizontal partition wall sub-dividing the hollow space of the hollow body into at least two relatively smaller hollow space, and wherein one or more surfaces of the partitioning element is mounted with one or more UV LED arrays.

2. The apparatus of claim 1, wherein the cross-section of the hollow body is triangular, square, or polygonal shape including pentagon, hexagon and octagon, and each of the at least two open ends of the hollow body has a shape corresponding to one end of the pipe structure so as to avoid leakage of any medium passing through the connection between the one end of the pipe and the corresponding end of the hollow body.

3. The apparatus of claim 1, further comprising an indicator connected to the control module to generate a signal indicating the UV module is under operation and/or sense an object approaching an operating UV module of the apparatus to generate a warning signal to an operator or user of the apparatus.

4. The apparatus of claim 3, wherein the signal comprises audio and visual signals.

5. The apparatus of claim 3, wherein the signal is digital or analog signal.

6. The apparatus of claim 1, wherein the partitioning element is composed of at least two partition walls, and wherein two of the partition walls are extended from four different points on the inner surface of the hollow body and intersect with each other along the central axis of the hollow body to form an inter-cross supporting element.

7. The apparatus of claim 1, further comprising at least one heat dissipating element being positioned on the outer surface of the hollow body.

8. The apparatus of claim 1, wherein the partitioning element is composed of more than two of the partition walls such that the hollow space of the hollow body is sub-divided by the partitioning element into more than two relatively smaller hollow spaces.

9. The apparatus of claim 7, wherein the at least one heat dissipating element comprises one or more heat sinks, a liquid-based cooling system, or both.

10. The apparatus of claim 1, wherein the inner surface is UV-reflective.

11. The apparatus of claim 1, further comprising an inner pipe structure situated in the interior of the hollow body, wherein the inner pipe structure is made of a material which allows the UV lights from the UV LED arrays to pass through the wall of the inner pipe structure without any loss of energy to disinfect the medium passing through the interior space of the inner pipe structure.

12. A food and beverage processor comprising at least one pipe structure and the apparatus of claim 1 for disinfecting an edible medium passing through a connection between said at least one pipe structure and the apparatus of claim 1 by UV radiation from the UV module of the apparatus while the flow rate of the edible medium and operational temperature of the processor remains constant throughout the disinfecting process of the edible medium.

13. A plumbing and drainage system comprising at least one pipe structure and the apparatus of claim 1 for disinfecting a medium passing through a connection between said at least one pipe structure and the apparatus of claim 1 by UV radiation from the UV module of the apparatus while the flow rate of the medium and the temperature of the plumbing and drainage system remains constant throughout the disinfecting process of the medium.

14. An disinfection system comprising at least one pipe structure and the apparatus of claim 1 for disinfecting a medium passing through a connection between said at least one pipe structure and the apparatus of claim 1 by UV radiation from the UV module of the apparatus while the flow rate of the medium and the temperature of the disinfection system remains constant throughout the disinfecting process of the medium, wherein said medium comprises gas, liquid, solid, or any combination thereof.

15. A method for disinfecting an edible medium in a manufacturing process thereof comprising exposing the edible medium to a UV source during transportation from a pipe structure to another pipe structure of a food or beverage processor through a connection between two pipe structures, wherein the connection comprises the apparatus of claim 1.

16. A method for disinfecting a medium during wastewater or sewage treatment comprising exposing the medium to a UV source during transportation from a pipe structure to another pipe structure of a wastewater or sewage treatment system through a connection between two pipe structures, wherein the connection comprises the apparatus of claim 1.

17. An ultraviolet disinfection apparatus comprising:
a hollow body comprising a cross-section and at least two open ends, each of the at least two open ends communicating with one end of a pipe structure, and further comprising an inner surface and an outer surface, the inner surface including one or more interior structures which is flat or curved, the one or more interior structures being defined by one or more partitions situated in part or in full length along the inner surface of the hollow space;
an ultraviolet (UV) module comprising one or more UV LED arrays independently or severally arranged with each other, the one or more UV LED arrays being mounted on the flat or curved surface of the interior structures;
a control module being connected to the UV module and located remotely from the hollow body of the apparatus; and
further comprising at least one heat dissipating element positioned on the outer surface of the hollow body.

18. An ultraviolet disinfection apparatus comprising:
a hollow body comprising a cross-section and at least two open ends, each of the at least two open ends communicating with one end of a pipe structure, and further comprising an inner surface and an outer surface, the inner surface including one or more interior structures which is flat or curved, the one or more interior structures being defined by one or more partitions situated in part or in full length along the inner surface of the hollow space;
an ultraviolet (UV) module comprising one or more UV LED arrays independently or severally arranged with each other, the one or more UV LED arrays being mounted on the flat or curved surface of the interior structures;
a control module being connected to the UV module and located remotely from the hollow body of the apparatus; and
further comprising an inner pipe structure situated in the interior of the hollow body, wherein the inner pipe structure is made of a material which allows the UV light from the UV LED arrays to pass through the wall of the inner pipe structure without any loss of energy to disinfect the medium passing through the interior space of the inner pipe structure.

* * * * *